(12) United States Patent
Vanderby et al.

(10) Patent No.: US 9,386,965 B2
(45) Date of Patent: Jul. 12, 2016

(54) ULTRASOUND MACHINE PROVIDING COMPOSITE IMAGE DATA

(71) Applicant: Wisconsin Alumni Research Foundation, Madison, WI (US)

(72) Inventors: Ray Vanderby, Madison, WI (US); Mon-Ju Wu, Madison, WI (US); Joseph Karls, Fitchburg, WI (US); Sarah Kuehl, Madison, WI (US); William A. Sethares, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 508 days.

(21) Appl. No.: 13/916,171

(22) Filed: Jun. 12, 2013

(65) Prior Publication Data

US 2014/0371587 A1  Dec. 18, 2014

(51) Int. Cl.
| | |
|---|---|
| G06K 9/00 | (2006.01) |
| A61B 8/08 | (2006.01) |
| G06T 7/00 | (2006.01) |
| A61B 8/00 | (2006.01) |
| A61B 8/14 | (2006.01) |

(52) U.S. Cl.
CPC ............ *A61B 8/5253* (2013.01); *A61B 8/5246* (2013.01); *G06T 7/0036* (2013.01); *A61B 8/0891* (2013.01); *A61B 8/14* (2013.01); *A61B 8/463* (2013.01); *A61B 8/485* (2013.01); *G06T 2207/10016* (2013.01); *G06T 2207/10132* (2013.01); *G06T 2207/20021* (2013.01); *G06T 2207/30004* (2013.01)

(58) Field of Classification Search
USPC .................................................. 382/128–134
See application file for complete search history.

(56) References Cited

U.S. PATENT DOCUMENTS

| 5,655,535 | A | * | 8/1997 | Friemel | A61B 8/0866 128/916 |
|---|---|---|---|---|---|
| 5,899,861 | A | * | 5/1999 | Friemel | A61B 8/4254 128/916 |
| 2004/0054281 | A1 | * | 3/2004 | Adam | A61B 8/587 600/437 |
| 2007/0036402 | A1 | * | 2/2007 | Cahill | G06T 7/0012 382/128 |
| 2008/0146932 | A1 | * | 6/2008 | Chalana | A61B 5/204 600/447 |
| 2010/0063393 | A1 | * | 3/2010 | Moradi | A61B 8/0833 600/442 |

OTHER PUBLICATIONS

Patrick Vandewalle, Sabine Susstrunk, Martin Vetterli; A Frequency Domain Approach to Registration of Aliased Images with Application to Super-resolutron; EURASIP Journal on Applied Signal Processing, 2006; pp. 1-14; vol. 2006; Article ID 74159; Hindawi Publishing Company; Europe.

Tuan C. Pham, Lucas J. Van Vliet, Klamer Schutte; Robust Fusion of Irregularly Sampled Data Using Adaptive Normalized Convolution; EURASIP Journal on Applied Signal Processing; 2006; pp. 1-13; vol. 2006; Article ID 83268; Hindawi Publishing Company; Europe.

* cited by examiner

*Primary Examiner* — Alex Liew
(74) *Attorney, Agent, or Firm* — Boyle Fredrickson, S.C.

(57) ABSTRACT

An ultrasound imaging system combines successive images of a time series to produce high-resolution ultrasound. A piecewise registration process and deemphasizing of high-frequency spatial components may be used to aid in the combination process. A high-definition image may be obtained with or separately from this process by combining different images obtained with different ultrasound frequencies. The images are weighted to accentuate the contribution of high-frequency ultrasound data at the leading edge of imaged structure.

13 Claims, 5 Drawing Sheets

ULTRASOUND MACHINE PROVIDING COMPOSITE IMAGE DATA

This invention was made with government support under EB008548 awarded by the National Institutes of Health. The government has certain rights in the invention.

STATEMENT REGARDING FEDERALLY SPONSORED RESEARCH OR DEVELOPMENT

--

CROSS REFERENCE TO RELATED APPLICATION

--

BACKGROUND OF THE INVENTION

The present invention relates to ultrasonic imaging equipment and, in particular, to a method and apparatus providing higher quality ultrasound images by combining data from several time displaced and/or several frequency displaced images.

Ultrasonic imaging provides a mapping of ultrasonic echo signals to an image plane where the magnitude of the reflected ultrasound wave ("echo") is mapped to brightness of pixels in the image. Such images may reveal structures within the body as delineated by the increased reflection that occurs at the interface between materials of dissimilar acoustic properties, for example, different tissue types.

Greater insight into the physical properties of the material being imaged may be obtained by using the ultrasound images for elasticity measurements. In one type of elasticity measurement termed "quasi-static elastography", two images of a material in two different states of deformation are compared. The material may be deformed by compression with the ultrasound probe itself, for example, or by the internal muscular forces, for example the patient stretching a tendon or the beating of a heart in medical imaging. Strain is deduced from these two images by computing gradients of the relative shift of the material in the two images along the deformation axis and the elasticity is deduced from this strain with an assumption about the applied force. Elastography in medical imaging is analogous to a physician's palpation of tissue during which the physician determines stiffness by finger pressure and detects the amount of material yield (strain) under this pressure.

Multiple ultrasound images, obtained rapidly in succession at different times, can provide ultrasonic video whose time dimension offers additional insight into the material being imaged. In theory, successive frames of ultrasound video can also provide for additional spatial information, for example, by combining the data of separate images into a higher resolution image. In practice, combining ultrasonic images to produce higher-quality images has been difficult to achieve.

SUMMARY OF THE INVENTION

The present inventors have identified and addressed a number of obstacles to combining ultrasonic data from multiple ultrasonic images into a higher-quality combination image. These obstacles include: (1) motion among structures in the material being imaged, this intra-image motion undercutting the assumption that the images are related in a single affine mapping (that is, are related to each other by simple rotation, translation or scale changes) and (2) the lack of well-defined image corners or other consistent registration features allowing the images to be properly aligned before combination.

The problem of intra-image motion is addressed by subdividing each of the images into portions that are then separately registered. In this way the assumption of affine transformations can be piecewise correct. Independent registration of these portions is accommodated by an interpolation process when the portions are combined.

The difficulties of registering ultrasound images are addressed by a registration process that deemphasizes spatial high-frequency data (e.g. ultrasound speckle) and image corners, with a broad area comparison that may be facilitated by performing the registration in the frequency domain.

The inventors have extended this technique of combining ultrasound images beyond combining images that are displaced in time to also include combining images obtained at different ultrasound frequencies. In combining these latter, "frequency-displaced" images, the inventors have accommodated the properties of ultrasound waves at lower frequencies traveling further into the tissue but contributing less detail to the image, and of higher frequencies traveling less deeply into the tissue before significant damping but providing more image detail. Accordingly, higher frequency image data are given greater weighting at short acoustic distances from the ultrasound transducer than lower frequency image data in the combination process.

Specifically then, in one embodiment, the present invention provides an ultrasonic imaging apparatus having an ultrasound transducer for transmitting ultrasound and detecting ultrasonic echoes from the transmitted ultrasound. The ultrasound transducer is connected to the ultrasound processing circuitry including an electronic computer executing a stored program to generate a series of time displaced images depicting ultrasound echo information over at least two dimensions of an imaged object and to combine multiple time displaced images to produce a high-resolution image. This combining process includes the steps of (i) subdividing each of the multiple time displaced images into multiple regions having at least two dimensions to provide corresponding regions in each of the multiple time displaced images; (ii) separately registering corresponding regions of the multiple time displaced images in rotation and translation; and (iii) combining the corresponding regions as registered to produce the high-resolution image.

It is thus a feature of at least one embodiment of the invention to provide a method of combining ultrasound images in which different image components may have separate motions while accommodating the assumption of images that are related by an affine transformation through the implementation of a piecewise approximation.

The combining may further include filtration of the corresponding image portions before registration to remove influence of high spatial frequency components of the corresponding image portions.

It is thus a feature of at least one embodiment of the invention to provide improved registration of ultrasound images having high-frequency speckle type noise.

The registration in translation may shift corresponding image portions to reduce differences in values of Fourier phase coefficients in the corresponding image portions. In this regard, the registration in translation may substantially disregard values of Fourier amplitude coefficients (especially those in the high frequency regions) in the corresponding image portions.

It is thus a feature of at least one embodiment of the invention to provide a registration process with reduced susceptibility to artifacts such as speckle noises that may be found in ultrasound images.

The registration may convert corresponding image portions into a frequency domain and register the corresponding image portions by determining a spatial offset needed to reduce differences in phase components of the frequency domain representations of the corresponding image portions.

It is thus a feature of at least one embodiment of the invention to provide an alignment mechanism that is more tractable, computationally, by operating in the frequency domain.

The registration of the corresponding images rotatively may shift corresponding image portions into registration to minimize differences in values of Fourier amplitude coefficients in the corresponding image portions.

It is thus a feature of at least one embodiment of the invention to provide a rotational alignment mechanism that may isolate the effects of rotation and scaling from translation, each of which may have different degrees of influence in time-shifted ultrasound images.

The registration in rotation may convert corresponding image portions into a frequency domain and register the corresponding image portions by determining a rotational, offset needed to reduce differences in amplitude components of the frequency domain representations of the corresponding image portions.

It is thus a feature of at least one embodiment of the invention to provide a rotational alignment mechanism that may take advantage of Fourier transformations of the images used in other registration processes.

The process of combining multiple time displaced images may be repeated with successive sets of time displaced images each within a rolling window of time covering a predetermined number of time displaced images shifted by an integer number of time displaced images with each repetition to provide a set of time displaced high-resolution images.

It is thus a feature of at least one embodiment of the invention to provide for high-resolution video output.

The corresponding regions may be identical in size and shape and regularly tile the dimension of each time displaced image.

It is thus a feature of at least one embodiment of the invention to provide a simple partitioning mechanism that does not require recognition or segmentation of the image by tissue type.

The electronic computer may further operate to repeat the combining to provide at least two high-resolution images and to compare the two high-resolution images to deduce a shifting of structure within the two high-resolution images to provide an output indicating elasticity of structure of the imaged object.

It is thus a feature of at least one embodiment of the invention to provide improved accuracy in elasticity tissue measurement using ultrasound. The present inventors have determined that the apparent visual improvement in resolution is not simply cosmetic but results in higher accuracy measurements to determine elasticity.

In one embodiment, the invention may provide an ultrasound transducer for transmitting ultrasound and detecting ultrasonic echoes from the transmitted ultrasound at multiple different ultrasonic frequencies and the ultrasound processing circuitry may include an electronic computer executing a stored program to generate at least two images depicting ultrasound echo information over at least two dimensions of an imaged object at different ultrasound frequencies, and to combine the images at the different ultrasound frequencies to produce a higher-definition image. This combining may weight the images to emphasize data from at least one image at a higher ultrasound frequency with respect to data from at least one image at a lower ultrasound frequency for portions of the high-resolution image closer to the ultrasound transducer and to deemphasize data from at least one image at higher ultrasound frequencies with respect to data from at least one image at lower ultrasound frequencies for portions of the high-resolution image further from the ultrasonic transducer.

It is thus a feature of at least one embodiment of the invention to extract additional information from images taken at different frequencies, in addition to or instead of images taken at different times, to provide for improved image quality.

The ultrasonic imaging apparatus may further perform the step of acquiring a time series of images at the different ultrasound frequencies to provide high-definition images at different times and include the step of combining multiple high-definition images acquired at different times to produce a high-resolution, high-definition image.

It is thus a feature of at least one embodiment of the invention to provide multiple sources of additional image data for improved image quality.

The weighting of the images in combining images obtained at different ultrasound frequencies may provide a weighting dependent on a cumulative value of attenuating tissue traversed by the ultrasound beam in passing from the ultrasonic transducer to material located at a point of the given data.

It is thus a feature of at least one embodiment of the invention to provide a method of favoring high-frequency ultrasound data at the leading edges of structure regardless of absolute depth of the structure.

These particular objects and advantages may apply to only some embodiments falling within the claims and thus do not define the scope of the invention.

DETAILED DESCRIPTION OF THE PREFERRED EMBODIMENT

Figure 1:
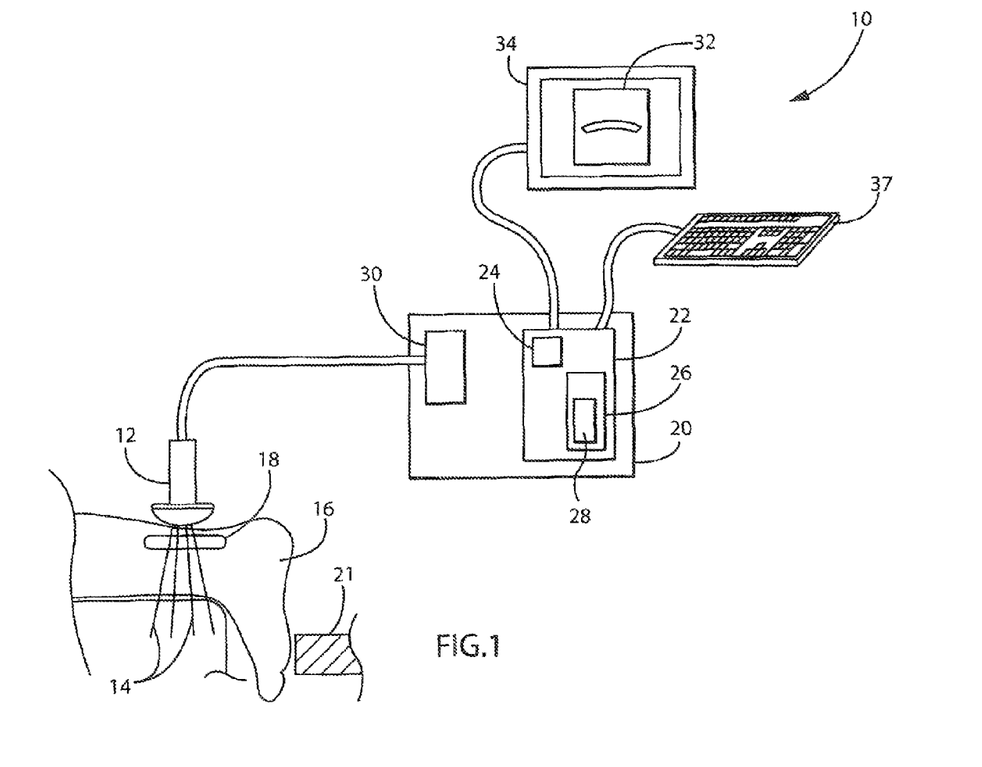
FIG. 1 is a simplified diagram of an ultrasound imaging system of a type suitable for use with the present invention, as depicted during imaging of structure such as a tendon for elasticity measurements of that tendon under different tensions.

Referring now to FIG. 1, an ultrasound system 10 suitable for use with the present invention may provide an ultrasound transducer 12, for example, providing for a linear array of transducer elements that may transmit laterally displaced ultrasound beams 14 through tissue 16 of the patient including, for example, a tendon 18.

The ultrasound beams 14 may travel through the tissue 16 and be reflected back to the ultrasound transducer 12 to be received thereby, converted to electrical signals, and transmitted to a processing unit 20.

The processing unit 20 may include, for example, an electronic computer 22 having a processor 24 communicating with a memory 26 holding a stored program 28. A graphic display 34 for displaying images generated by the processing unit 20 may communicate with the processing unit 20. In addition, a user input device 37 such as a keyboard and/or mouse or equivalent may allow for the entry of data by the user to the processing unit 20. Execution of the stored program 28, according to techniques generally understood in the art, may generate digital signals to interface electronics 30 that provide the necessary electrical signals to the transducer 12 to generate the ultrasound beams 14. Interface electronics 30 may then receive the echo signals from the transducer 12 and convert them to digital signals for processing by the electronic computer 22.

Also according to conventions generally understood in the art, the echo signals received from the transducer 12 may be processed by the processing unit 20 to produce an ultrasonic B-mode image 32 on the graphic display 34. The B-mode image 32 represents rows and columns of echo data with the rows correspond generally to depths along individual ultrasound beams 14 and the columns correspond to different laterally displaced ultrasound beams 14. As used herein, the term "image" 32 will refer both to the visual representation of data and the underlying data of that image.

The transducer 12 may be operated at different ultrasound frequencies either sequentially or in parallel so that multiple images 32 may be obtained each associated with a different ultrasound frequency. For example, images may be obtained at 8, 10, 12 and 13 megahertz. It will be understood that the B-mode echo images depict a magnitude of the returned ultrasonic echo signal being an amplitude envelope largely indifferent to the echo frequency.

In addition, multiple images 32 may be obtained over time to produce a time series of images in the manner of ultrasound video. These images may be stored in the memory 26 for later processing by the processor 24 according to the stored program 28.

Referring still to FIG. 1, the ultrasound, system 10 may be used to provide elasticity images using, for example, the quasi-static approach. In this example, a first set of images 32 of tendon 18 may be obtained with the tendon 18 in a relaxed state. A second set of images 32 may then be obtained in which the patient tensions the tendon 18, for example, by pressing the ball of the foot against a surface 21. As will be discussed below, the program 28 may combine the images of each set and then analyze movement of the tissue 16 between the combined images of the two states of deformation to establish tissue elasticity using known techniques where greater deformation of the tissue between the two images generally indicates relatively greater elasticity.

Figure 2:
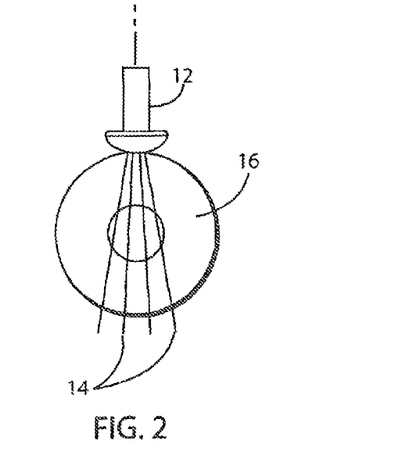
FIG. 2 is a fragmentary view of the ultrasound imaging system of FIG. 1 depicted during imaging of a compressible structure, such as a breast, for elasticity measurements of breast tissue under different compressions.

Referring now to FIG. 2 in an alternative application, the ultrasound transducer 12 or another probe may be used to press down upon the tissue 16 to provide the deformation between the two analyzed sets of images: the first set of images with the transducer 12 resting lightly on the tissue and the second set of images with the transducer 12 pressing down into tissue 16 to introduce a stress field into that tissue.

Combination of Time Displaced Images

Figure 3:
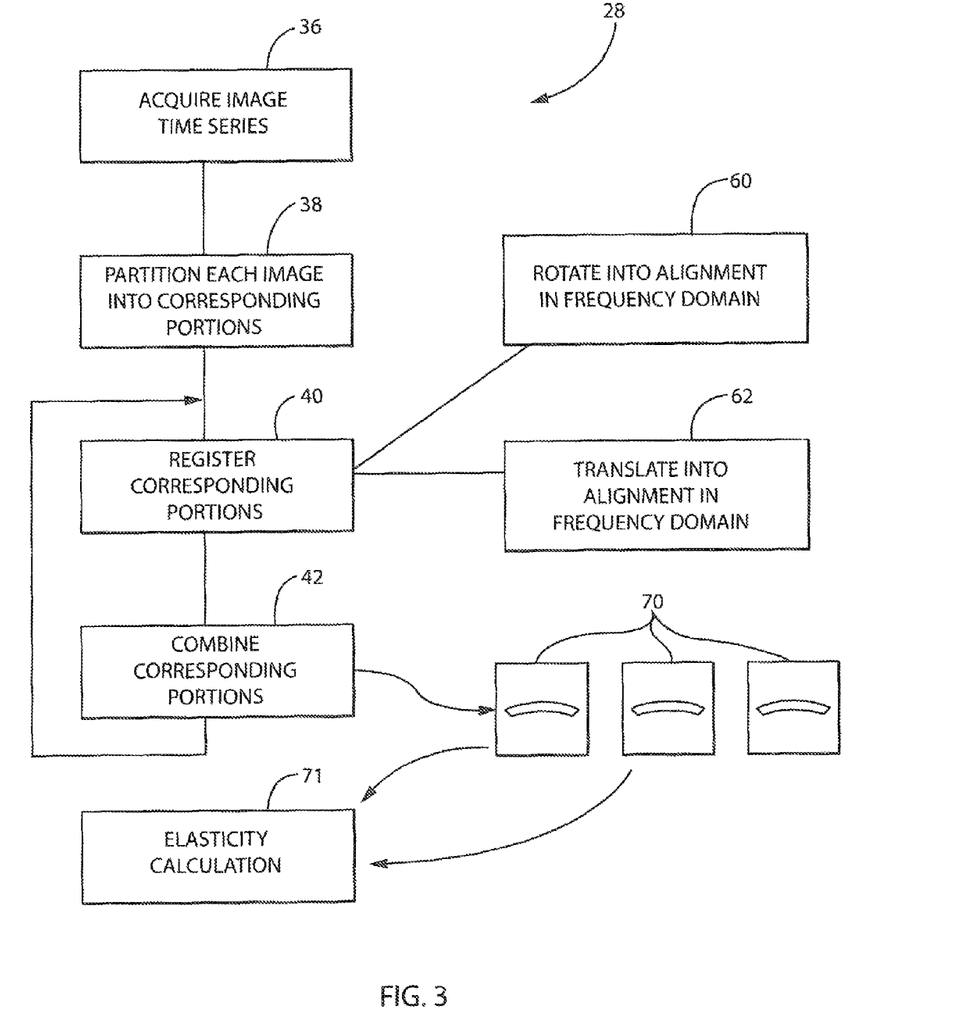
FIG. 3 is a flowchart of a program executed by the ultrasound imaging system of FIG. 1 showing steps in constructing a high-resolution ultrasound image.
Figure 4:
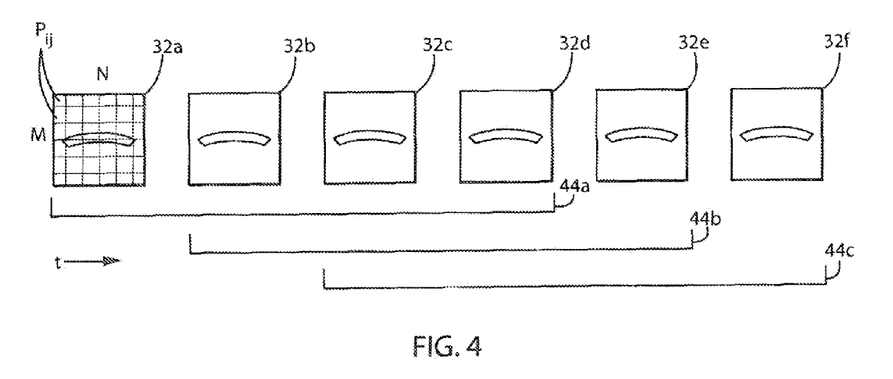
FIG. 4 is a representation of multiple successive frames of ultrasound video obtained with the apparatus of FIG. 1 during the imaging of either FIG. 1 or 2 according to the program of FIG. 3.

Referring now to FIGS. 3 and 4, the time series sets of images 32a-32f (shown in FIG. 4) each separated in time by a predetermined interframe period, for example one 50 th of the second, may be acquired as indicated by process block 36 of FIG. 3. Each image 32 provides a series of pixels providing data about the intensity of echo signal at corresponding volume elements within the tissue 16. In this example, the images are two-dimensional; however, it will be appreciated that the present invention may be readily expanded to three-dimensional processing.

At process block 38, each image is divided into corresponding portions $P_{i,j}$ where i is an index variable ranging over M rows of the image 32 and j is an index variable ranging over the N columns of the image 32. As depicted, the portions $P_{i,j}$ may each be defined by a set of regular rectangular tiles subdividing the image 32 into the M rows and N columns; however, other portion shapes which serve to tile over the image 32 without gaps (tessellate) can be envisioned. In one embodiment, each image is divided into 36 different portions $P_{i,j}$ forming six rows and six columns.

At the succeeding process blocks 40 and 42, subsets 44 of the time series images 32, each holding multiple images 32, will be registered with each other and then combined to produce a high-resolution image that may be output to the display 34 where it may be used for quantitative processing or for visual analysis by an expert (e.g., a radiologist). Desirably, a rolling series of subsets 44a-44c may be formed. In the example of the time series of images 32a-32f, a first subset 44a may be created holding four successive images 32a-32d, a second subset 44b holding four images 32b-32e, and each succeeding subset 44 adding one later image and dropping one earlier image. In this way a high-resolution images may be generated regularly at each video time interval to provide for, if desired, high-resolution video. It will be appreciated that the number of combined images 32 in each subset 44 may be readily varied as desired to include at least two images and preferably more than three images.

Referring still to FIG. 3, in the registration process of process block 40, each of the portions $P_{i,j}$ of each of the images in a subset 44 will be independently registered with corresponding portions $P_{i,j}$ in the other images of the subset 44. Typically this process will be performed on a pair-wise basis to register each portion $P_{i,j}$ of the different images with a given portion of a designated baseline image, for example, being the earliest image of the subset 44.

The registration process will generally involve determining the relative translation and rotation of each portion $P_{i,j}$ with respect to its corresponding portion in the baseline image and then shifting and rotating that portion $P_{i,j}$ according to the relative translation and rotation so that the two portions align and can be combined. Corresponding portions $P_{i,j}$ are portions that approximately cover the same structure within the tissue 16 and, in the embodiment described, will be identified as having identical rows and columns (i, j) within the image 32.

Figure 5:
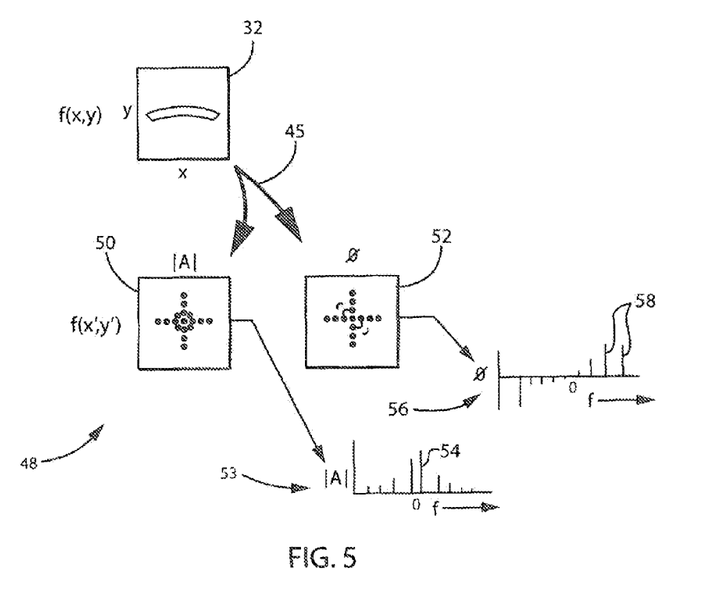
FIG. 5 is a diagrammatic representation of a two-dimensional Fourier transform that may be applied to successive frames of FIG. 4 showing separate amplitude and phase coefficient images.

In one embodiment, this registration process is performed in the frequency domain. Referring to FIG. 5, each image 32 may generally have spatial coordinates of rows and columns designated y and x according to standard Cartesian notation. A Fourier transform 45 of the image 32 may be performed to provide for a frequency domain image 48 usefully decomposed into a Fourier magnitude image 50 and a Fourier phase image 52 representing the corresponding magnitude and phase coefficient of the Fourier transform. The Fourier magnitude image 50 provides a measure of the spectral energy of the image 32, for example, a single row 53 of the Fourier magnitude image 50 having magnitude values 54 representing the spectral energy at different spatial frequencies. Generally images 32 that approximate slowly changing shade gradients will have higher values toward the center of each row 53 representing lower spatial frequencies (assuming the zero frequency point of the row is centered in the row) whereas images 32 that have high levels of rapidly changing detail will have higher values toward the left and right edges of each row representing higher spatial frequencies.

The Fourier phase image 52 provides a relative phase offset of the frequencies of the Fourier magnitude image 50, for example, a single row 56 having phase values 58 representing the phase of the corresponding magnitude values 54.

Figure 6:
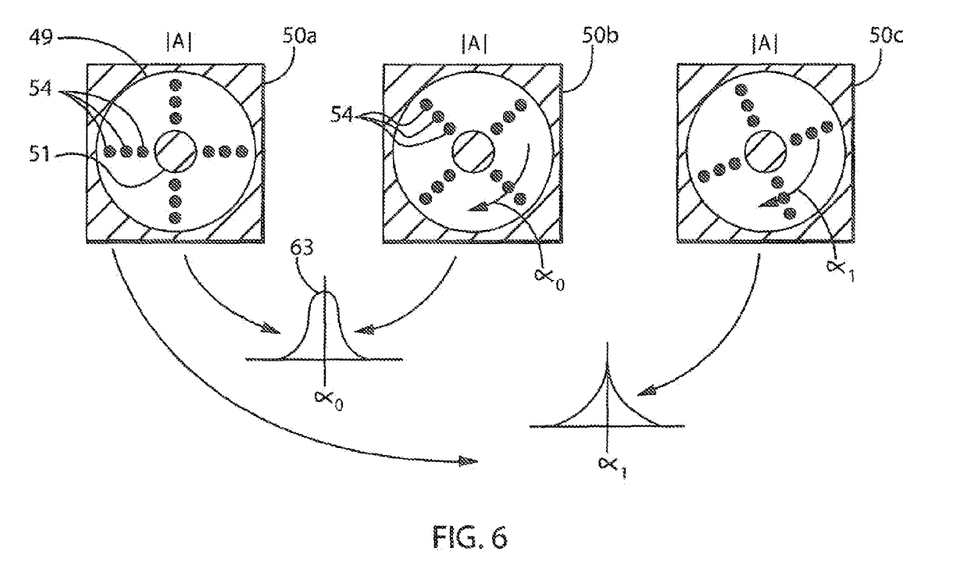
FIG. 6 is a diagrammatic representation of rotational registration using the amplitude coefficient images of FIG. 5.

Referring now to FIGS. 3 and 6, in the first step in the registration process of process block 40, as indicated by subprocess block 60, the corresponding portions P of the images of the subset 44 are registered with respect to rotation. This process may compare Fourier magnitude image 50a of a portion $P_{i,j}$ of image 32a with Fourier magnitude image 50b of a portion $P_{i,j}$ of image 32b, for example, to deduce the rotatable offset between the two. In this process, each Fourier magnitude image 50 is first windowed to a circular window 49 centered about the zero frequency position (for example, using a Tukey window sized to fit within a circle circumscribed by the boundaries of the Fourier magnitude image 50). In addition, the "DC values" 51 about the origin of each Fourier magnitude image 50 (at approximately 1/10 the radius of the Tukey window) representing low spatial frequencies are removed.

As windowed, the Fourier magnitude image 50b is incrementally rotated about its origin by angle alpha and the correlation between the images 63 as a function of alpha is measured to find a peak correlation value ($\alpha$0) that will be used to rotate portion $P_{i,j}$ image 32b with respect to portion $P_{i,j}$ image 32a before combination. Typically a full range of angles alpha need not be investigated based on an assumption that the portions $P_{i,j}$ remain relatively aligned in rotation. This process is then repeated for each of the portions $P_{i,j}$ independently to determine a rotational offset for the portions $P_{i,j}$ of each of images 32b-32d with respect corresponding portions $P_{i,j}$ of image 32a. So, for example, the process may be repeated for the next portions $P_{i,j}$ of the Fourier magnitude image 50a and Fourier magnitude image 50c corresponding to image 32a and image 32c to produce a value of rotatable offset of $\alpha$1. Ultimately this process allows the portions $P_{i,j}$ of each of images 32a-32c to be mutually registered in rotation. It will be appreciated that the windowing process of the Fourier magnitude images deemphasizes high spatial frequency information of the images 43 in the alignment process as well as very low spatial frequency information.

Figure 7:
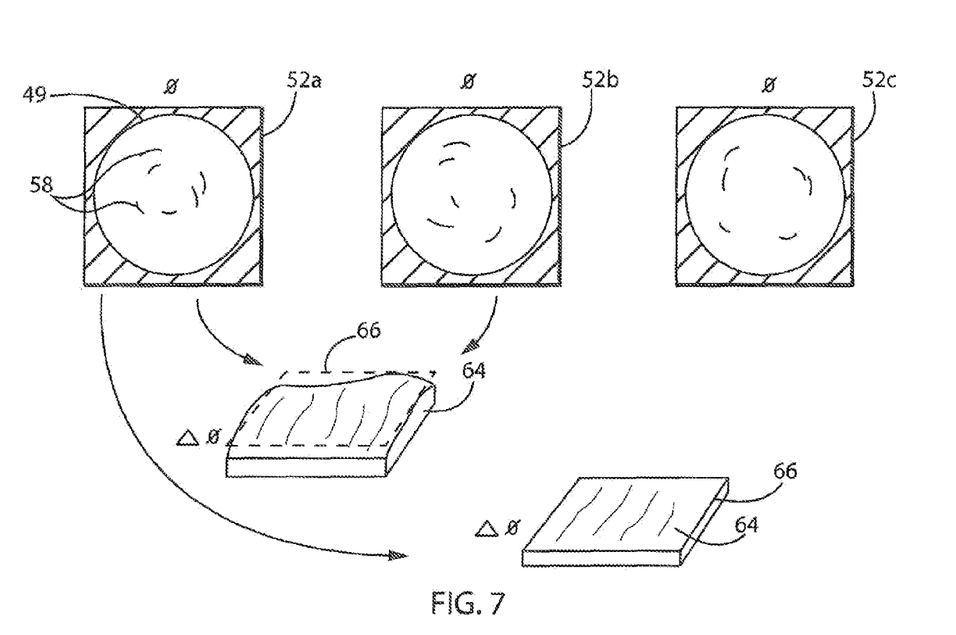
FIG. 7 is a figure similar to that of FIG. 6 showing translational registration using the phase coefficient images of FIG. 5.

Referring now to FIGS. 3 and 7, translated offsets along the x- and y-axes of images 32 may then be determined to register these images in translation per subprocess block 62. In this process, only the Fourier phase image 52a of the portions $P_{i,j}$ is considered after windowing as described above. As before, each of the images 32 will be pairwise translatively aligned to a baseline image, for example, being the first image in the subset 44.

In this translation process, a two-dimensional phase difference map 64 is generated between each corresponding pair of portions $P_{i,j}$ in two different Fourier phase images 52 representing a point wise difference between phase values 58 for corresponding points in the two portions $P_{i,j}$ of the two Fourier phase images 52. A plane 66 is then fit to the three-dimensional surface of the difference map 64 by a least-squares approximation and the average slope of this plane in the x and y directions is used to deduce the x and y offset between the portions $P_{i,j}$ of the corresponding images 32. As before, this process is repeated for successive Fourier phase images 52 so that each of the portions $P_{i,j}$ of each of the images 32 within the subset 44 may be aligned in translation to corresponding common portions $P_{i,j}$.

Referring still to FIG. 3, once each of the portions $P_{i,j}$ of each of the images 32 in the subset 44 is aligned in rotation and in translation, (by shifting according to the deduced offsets) they are combined by averaging together corresponding data points. Typically, the shifting and rotation of the registration process means that the data points for different portions $P_{i,j}$ will no longer lie on a common grid and accordingly bicubic interpolation or other similar interpolation (for example, normalized convolution) will be used to make this combination. The interpolated values to a common grid are then averaged together.

The result is a series of high-resolution image 70 associated with each subset 44 each separated in time by the interframe time of the images 32 but delayed by the number of images in a subset 44. This series of high-resolution images may then be displayed on display 34 as a high-resolution ultrasound video. Alternatively or in addition, high-resolution video images 70 associated with different deformations of the tissue may be used to compute elasticity value per process block 71 according to the quasi-static process described above or other elasticity calculating procedures known in the art. The elasticity calculation may be output as a numeric value, an image or a video image.

Combination of Frequency Displaced Images

Figure 8:
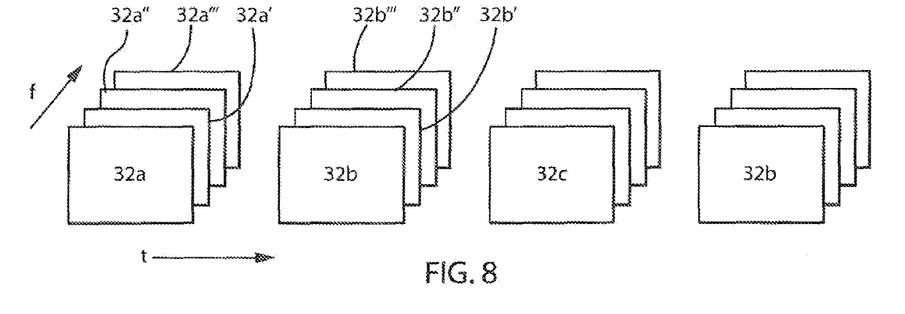
FIG. 8 is a figure similar to that of FIG. 4 showing the acquisition of augmenting images taken at different ultrasonic frequencies.

Referring now to FIG. 8, in a further embodiment, the present invention contemplates that additional image information may be obtained by obtaining images 32 at different times as before, and/or at different frequencies to provide for augmenting images 32', 32", 32'" (or more) for each image 32. Thus, for example, image 32a taken at 8 megahertz may be augmented with images 32'a, 32"a and 32'"a obtained at 10, 12 and 13 megahertz, respectively. These augmenting images 32 may be obtained, for example, by repeated scanning after the acquisition of each image 32 (after switching the ultrasound transducer 12 to another frequency), or simultaneously with the acquisition of each image 32 by broadband scanning with multiple frequencies through the transducer 12. The invention also contemplates that the order of the scanning may be varied such as to provide for first scanning of images 32a-32d of a subset 44 at a first frequency and then repeating that scanning for the augmenting frequencies.

Depending on the particular scanning approach, each image 32 and its augmenting images 32', 32", 32'" may be intrinsically registered (having been obtained at substantially the same time) or may be registered using the processes described above by partitioning each of the images 32 into partitions $P_{i,j}$ and performing the registration on each partition per process blocks 38, 40 (including process blocks 60 and 62) and process block 42. Alternatively, each of the images at a given frequency may be first combined (for example, combining 32*a*-32*d*, augmenting images 32'*a*-32'*d*, etc.) and then the combined images may be combined.

In all cases, the combination of the images 32 associated with different frequencies will differ from the previous combination process primarily by the addition of a weighting of each of the augmenting images before the combination. A first step in this weighting provides a normalizing weighting to each image and its augmenting images to compensate for the fact that echo energies at different frequencies may differ substantially with lower frequency images and are usually brighter than those of higher frequency images. For example, for images $f_8$, $f_{10}$, $f_{12}$ and $f_{13}$, representing images 32, 32', 32'', and 32''' respectively, the following weighting system can be adopted:

$$\hat{f}_8(i,j) = \frac{\sum_{i,j} f_{13}(i,j)}{\sum_{i,j} f_8(i,j)} f_8(i,j) \tag{1}$$

$$\hat{f}_{10}(i,j) = \frac{\sum_{i,j} f_{13}(i,j)}{\sum_{i,j} f_{10}(i,j)} f_{10}(i,j) \tag{2}$$

$$\hat{f}_{12}(i,j) = \frac{\sum_{i,j} f_{13}(i,j)}{\sum_{i,j} f_{12}(i,j)} f_{12}(i,j) \tag{3}$$

$$\hat{f}_{13}(i,j) = f_{13}(i,j) \tag{4}$$

to produce normalized images $\hat{f}_8$, $\hat{f}_{10}$, $\hat{f}_{12}$ and $\hat{f}_{13}$. Normalization, as used herein, means adjusting values to a common scale and does not require that common scale to be from 0 to 1.

Many such weighting schemes are possible: the key idea is that the scheme should weight high frequency measurements near the transducer and low frequency measurements further form the transducer.

Figure 9:
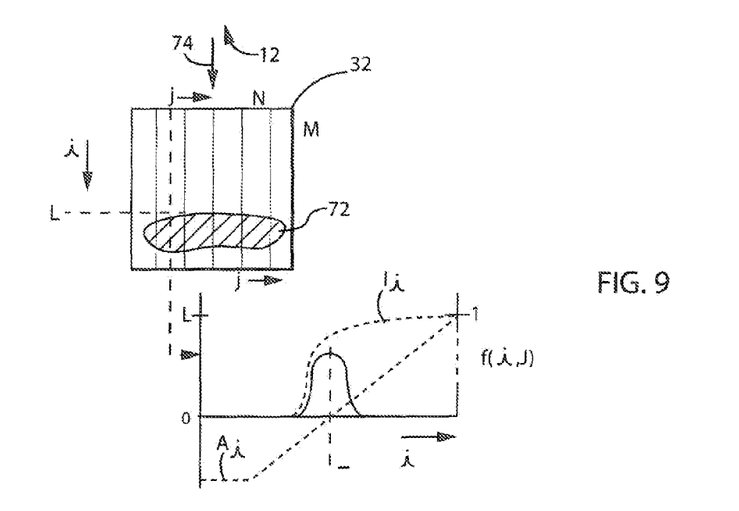
FIG. 9 is a representation of one image of FIG. 8 showing the development of weights used to combine the multiple frequency images.

Referring now to FIG. 9, a second level of contribution weighting of each of these weighted images is then performed to accentuate the image data taken at higher frequencies at leading edges of attenuating structures 72 in the image 32. This leading edge is determined by a direction 74 of ultrasound propagation and for that reason will be the edge closest to the ultrasound transducer 12.

This contribution weighting is facilitated by calculation of two values $I_i$ and $A_{i,j}$. Value $I_i$ expresses the cumulative intensity of the echo image along each column and value $A_{i,j}$ captures a depth into the attenuating structure 72 as follows:

$$I_i = \frac{\sum_{i=1}^{i=l} f(i,j)}{\sum_{i=1}^{i=N} f(i,j)} \tag{5}$$

$$A_{i,j} = \frac{i-L}{M-L} \tag{6}$$

where M and N are the number of rows and columns of the image a and L is the row number for column J at which f(i, j) is maximum.

As will be appreciated, equation (5) basically integrates the intensity of the echo values as one moves down each column rising between zero and a maximum of 1. Equation (6) roughly provides a depth value increasing as one moves deeper into the most attenuating structure of the given row.

One possible weighting system using the above values is provided as follows:

$$\bar{f}(i,j) = f_R(i,j) + \sum_{r=1}^{R-1} \left[ A_{i,j} + \left(\frac{r-1}{R-2}\right)(1-2A_{i,j}) \right] I_i f_r(i,j) \tag{7}$$

where R an index indicating the particular frequency rank (8-13 megahertz).

For the particular frequencies described above this becomes:

$$\tilde{f}(i,j) = f_{13}(i,j) + (1-A_{i,j})I_i f_{12}(i,j) + 0.5 I_i f_{10}(i,j) + A_{i,j} I_i f_8(i,j) \tag{8}$$

These weighted values are then combined after appropriate registration of the given portions $P_{i,j}$ by an averaging after appropriate interpolation.

Figure 10:
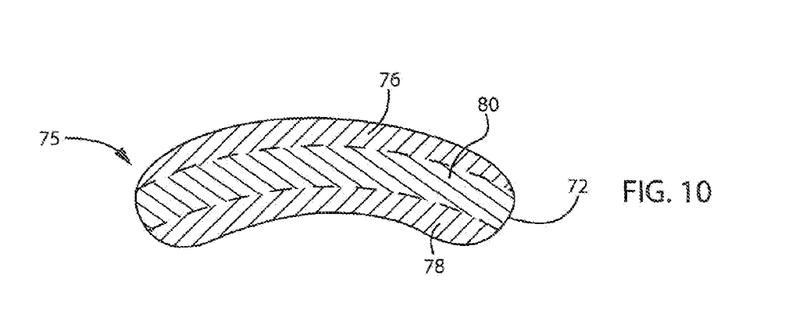
FIG. 10 is a representation of an image structure showing regions with different frequency contributions based on the weighting of FIG. 9.

Referring now to FIG. 10, generally this weighting system provides what will be termed for convenience a high-definition image 75 in which an image of structure 72 will have a first leading region 76 in which higher frequencies (e.g. $f_{13}$) dominate in formation of the image and a trailing region 78 where lower frequencies (e.g. $f_8$) dominate in formation of the image separated by a transition region 80 with more equal contributions. This weighting system provides greater sharpness at the leading edge of structure 72 while improving the information content deeper into the structure 72.

Generally it will be understood that the high-definition image 75 also provides for higher resolution as a result of the combination of additional image data and the term high-definition is used merely for clarity in discussing these different mechanisms of time and frequency displaced image combination.

As noted above, the order in which the multiple augmenting images and multiple time-displaced images are combined may be varied and, for example, combination of the multiple augmenting images may be performed before or after combination of images taken at different times. In addition, the invention contemplates that the weighting process may be varied to be performed before or after registration. The result will be a set of high-resolution, high-definition images that may be used to provide ultrasound video or for the purposes of elastography or other qualitative or quantitative purposes.

Example I

Three porcine digital flexor tendons, completely excised from surrounding tissue but with an intact bone-tendon insertion site, were mechanically tested in a servohydraulic test system (MTS 858, Minneapolis, USA). Original tendon length was recorded for strain calculations. A bead of graphite-impregnated silicone gel was placed on the surface of the tendons to provide a non-deforming image segment.

Tendons were incrementally stretched, 0.1 mm at a time, inside a saline-filled bath (which facilitated transmission of ultrasound waves), to a non-damaging physiological strain (<6.5% strain). Four ultrasound images, one each at 8, 10, 12, and 13 MHz, were captured at each stretch increment (GE Logiqe, Fairfield, USA). Unprocessed images were combined into four videos (one at each frequency) to produce "raw video." Images were subjected to processing to produce a high-resolution image followed by a combination of high-resolution images into high-definition images as discussed above to produce "processed video 1". The raw video was then combined in the alternative order to first produce high-definition video and then combine the high-definition video into high-resolution video to produce "processed video 2". Each of processed video 1 and processed video 2 was loaded into a custom DIC-tracking algorithm to calculate average strain in the tissue. Accuracy of the strain values was measured by comparison to the actual strain value, and precision of the strain values was measured by calculating the coefficient of variation.

Tendon strain measurements in raw and processed videos are summarized in Table 1. Tendons 1, 2, and 3 were stretched to strains of 4.68-6.43%. DIC strain measurements using raw videos ranged from 5.34-9.67%, whereas measurements using processed video 1. and processed video 2 ranged from 4.38-6.65%.

TABLE 1

|          |        | 8 MHz  | 10 MHz | 12 MHz | 13 MHz | Actual | Processed Video 1 | Processed Video 2 |
|----------|--------|--------|--------|--------|--------|--------|-------------------|-------------------|
| Tendon 1 | Strain | 8.84%  | 8.42%  | 8.90%  | 9.67%  | 6.43%  | 6.65%             | 6.60%             |
|          | CV     | 16.84% | 27.08% | 10.45% | 34.50% |        | 1.63%             | 1.34%             |
| Tendon 2 | Strain | 6.14%  | 5.69%  | 5.78%  | 6.57%  | 4.83%  | 5.14%             | 4.38%             |
|          | CV     | 53.33% | 33.51% | 33.98% | 17.74% |        | 9.52%             | 9.68%             |
| Tendon 3 | Strain | 7.39%  | 5.71%  | 7.47%  | 5.34%  | 4.68%  | 4.67%             | 4.68%             |
|          | CV     | 41.17% | 33.89% | 43.55% | 39.97% |        | 2.38%             | 11.10%            | where CV is coefficient of variation in strain measured in the raw and processed videos.

The results in Table 2 (below) demonstrate improved accuracy (as demonstrated by a reduced strain error; p=0.018, t-test comparison) and piecision (as demonstrated by a reduced coefficient of variation; p=0.018, t-test comparison) in the super-resolved images compared to raw videos.

TABLE 2

|          |                | Raw video | Actual | Average of processed video 1 and 2 |
|----------|----------------|-----------|--------|------------------------------------|
| Tendon 1 | Strain         | 8.96%     | 6.43%  | 6.63%                              |
|          | Strain Error % | 35.6%     |        | 3.3%                               |
|          | CV             | 22.22%    |        | 1.49%                              |
| Tendon 2 | Strain         | 6.05%     | 4.83%  | 4.76%                              |
|          | Strain Error % | 25.10%    |        | 1.40%                              |
|          | CV             | 34.64%    |        | 9.60%                              |
| Tendon 3 | Strain         | 6.48%     | 4.68%  | 4.68%                              |
|          | Strain Error % | 38.5%     |        | 0.10%                              |
|          | CV             | 39.65%    |        | 6.74%                              |
| Average  | Strain Error % | 33.1%     |        | 1.6%                               |
|          | CV             | 31.63%    |        | 5.85%                              |

Example II

A silicone breast tumor phantom (provided by SuperSonic Imagine, Aix-en-Provence, France) was mechanically compressed in a servohydraulic test system (MTS 858, Minneapolis, Minn., USA). The "breast" was incrementally compressed, 0.1 mm at a time, with the ultrasound transducer positioned immediately over the "tumor." Four ultrasound images, one each at 8, 10, 12, and 13 MHz, were captured at each compression increment. Unprocessed images were combined into four videos (one at each frequency); this is the "raw video." Raw video images were subjected to processing to produce a high-resolution image followed by a combination of high-resolution images into high-definition, high-resolution images as discussed above to produce "processed video 1". The raw video was then combined in the alternative order to first reduce high-definition video and then combine the high-definition video into high-definition, high-resolution video to produce "processed video 2".

Each of the videos (raw video, processed video 1 and processed video 2) was loaded into a custom DIC-tracking algorithm to calculate average strain in the tissue. Precision of the strain values was measured by calculating the coefficient of variation. These videos were also loaded into a custom segmentation algorithm to calculate ultrasound image brightness such that the brightness of the pixels inside the "tumor" region and in the surrounding "breast tissue" regions could be quantified and compared, in order to determine the contrast ratio between these two "tissue" types.

Variability in strain measurements of the compressed tumor phantom is demonstrated in Table 3.

TABLE 3

|    | 8 MHz  | 10 MHz | 12 MHz | 13 MHz | processed video 1 | processed video 1 |
|----|--------|--------|--------|--------|-------------------|-------------------|
| CV | 11.95% | 16.90% | 12.84% | 38.64% | 1.17%             | 1.18%             |

The average CV for raw videos was 20.62%, compared to an average CV value of 1.18% for processed videos. Thus, spatial and frequency-based high-definition, high-resolution of ultrasound images results in reduced variability in strain measurements in a tumor phantom.

The average contrast ratio in the raw videos was 2.43, while the contrast ratio in the processed videos was 3.38. Thus, spatial and frequency-based high-resolution, high-definition of ultrasound images results in improved contrast ratio in images of a breast tumor phantom.

The terms "high resolution", "higher resolution", "high definition" and "higher definition" as may be used herein refer generally to effective increases in resolution resulting from improved signal to noise ratio in the underlying data of the image that may result in one or both of practically increased spatial resolution or pixel depth resolution, the latter being the number of grey scale or color levels rendered by a pixel.

Certain terminology is used herein for purposes of reference only and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the and" "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a computer" and "a processor" can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. An ultrasonic imaging apparatus comprising:
an ultrasound transducer for transmitting ultrasound and detecting ultrasonic echoes from the transmitted ultrasound;
ultrasound processing circuitry including an electronic computer executing a stored program to:
(a) generate a series of time displaced images depicting ultrasound echo information over at least two dimensions of an imaged object; and
(b) combine multiple time displaced images to produce a high-resolution image with the steps of:
(i) subdividing each of the multiple time displaced images into multiple regions having at least two dimensions to provide corresponding regions in each of the multiple time displaced images;
(ii) separately registering corresponding regions of the multiple time displaced images in rotation and translation; and
(iii) combining the corresponding regions as registered to produce the high-resolution image;
wherein the combining further includes filtration of the corresponding image portions before registration to remove influence of high spatial frequency components of the corresponding image portions;
wherein the registration in translation shifts corresponding image portions to reduce differences in values of Fourier phase coefficients in the corresponding image portions;
wherein the registration in translation substantially disregards values of Fourier magnitude coefficients in the corresponding image portions; and
wherein the registration converts corresponding image portions into a frequency domain and registers the corresponding image portions by determining a spatial offset needed to reduce differences in phase components of the frequency domain representations of the corresponding image portions.

2. An ultrasonic imaging apparatus comprising:
an ultrasound transducer for transmitting ultrasound and detecting ultrasonic echoes from the transmitted ultrasound;
ultrasound processing circuitry including an electronic computer executing a stored program to:
(a) generate a series of time displaced images depicting ultrasound echo information over at least two dimensions of an imaged object; and
(b) combine multiple time displaced images to produce a high-resolution image with the steps of:
(i) subdividing each of the multiple time displaced images into multiple regions having at least two dimensions to provide corresponding regions in each of the multiple time displaced images;
(ii) separately registering corresponding regions of the multiple time displaced images in rotation and translation; and
(iii) combining the corresponding regions as registered to produce the high-resolution image;
wherein registration of the corresponding images rotatively shifts corresponding image portions into registration to minimize differences in values of Fourier magnitude coefficients in the corresponding image portions; and
wherein the registration converts corresponding image portions into a frequency domain and registers the corresponding image portions by determining a rotational offset needed to reduce differences in magnitude components of the frequency domain representations of the corresponding image portions.

3. An ultrasonic imaging apparatus comprising:
an ultrasound transducer for transmitting ultrasound and detecting ultrasonic echoes from the transmitted ultrasound;
ultrasound processing circuitry including an electronic computer executing a stored program to:
(a) generate a series of time displaced images depicting ultrasound echo information over at least two dimensions of an imaged object; and
(b) combine multiple time displaced images to produce a high-resolution image with the steps of:
(i) subdividing each of the multiple time displaced images into multiple regions having at least two dimensions to provide corresponding regions in each of the multiple time displaced images;
(ii) separately registering corresponding regions of the multiple time displaced images in rotation and translation; and
(iii) combining the corresponding regions as registered to produce the high-resolution image; and
wherein the process of combining multiple time displaced images to produce a high-resolution image is repeated with successive sets of time displaced images each within a rolling window of time covering a predetermined number of time displaced images shifted by an integer number of time displaced images with each repetition to provide a set of time displaced high-resolution images.

4. The ultrasonic imaging apparatus of claim 3 wherein the corresponding regions are identical in size and shape and regularly tile the dimension of each time displaced image.

5. The ultrasonic imaging apparatus of claim 3 wherein the electronic computer further operates to repeat the combining of step (b) to provide at least two high-resolution images and to compare the two high-resolution images to deduce a shifting of structure within the two high-resolution images to provide an output indicating elasticity of structure of the imaged object.

6. An ultrasonic imaging apparatus comprising:
an ultrasound transducer for transmitting ultrasound and detecting ultrasonic echoes from the transmitted ultrasound;
ultrasound processing circuitry including an electronic computer executing a stored program to:
(a) generate a series of time displaced images depicting ultrasound echo information over at least two dimensions of an imaged object; and
(b) combine multiple time displaced images to produce a high-resolution image with the steps of:
(i) subdividing each of the multiple time displaced images into multiple regions having at least two dimensions to provide corresponding regions in each of the multiple time displaced images;
(ii) separately registering corresponding regions of the multiple time displaced images in rotation and translation; and
(iii) combining the corresponding regions as registered to produce the high-resolution image; and
wherein step (a) generates a series of time and frequency displaced images depicting ultrasound echo information over at least two dimensions of an imaged object at different times and at different ultrasonic frequencies; and:
wherein step (b)(i) subdivides each of the multiple time displaced images into multiple regions having at least two dimensions to provide corresponding regions in each of multiple time and frequency displaced images; and further including the step of:
combining corresponding regions of frequency displaced images to emphasize data from regions associated with higher ultrasonic frequencies for portions of the combined high-resolution image closer to the ultrasound transducer over data from regions associated with lower ultrasonic frequencies and to deemphasize data from regions associated with higher ultrasonic frequencies for portions of the combined high-resolution image further from the ultrasound transducer over regions associated with lower ultrasonic frequencies.

7. An ultrasonic imaging apparatus comprising:
an ultrasound transducer for transmitting ultrasound and detecting ultrasonic echoes from the transmitted ultrasound at multiple different ultrasonic frequencies;
ultrasound processing circuitry including an electronic computer executing a stored program to:
(a) generate at least two images depicting ultrasound echo information over at least two dimensions of an imaged object at different ultrasound frequencies; and
(b) combine the images at the different ultrasound frequencies to produce a high-definition image with the steps of:
(i) weighting the images to emphasize data from at least one image at a higher ultrasound frequency with respect to data from at least one image at a lower ultrasound frequency for portions of the high-resolution image closer to the ultrasound transducer and to deemphasize data from the at least one image at higher ultrasound frequencies with respect to data from at least one image at lower ultrasound frequencies for portions of the high-definition image further from the ultrasound transducer; and
(ii) combining the multiple registered regions to produce the high-definition image.

8. The ultrasonic imaging apparatus of claim 7 further including the step of acquiring a time series of images at the different ultrasound frequencies to provide high-definition images at different times and including the step of combining multiple high-definition images acquired at different times to produce a high-resolution, high-definition image.

9. The ultrasonic imaging apparatus of claim 8 further including the steps of:
(i) subdividing each of the multiple high-definition images into multiple regions having at least two dimensions to provide corresponding regions in each of the multiple high-definition images;
(ii) separately registering corresponding regions of the multiple high-definition images acquired at different times in rotation and translation;
(iii) combining the corresponding regions as registered to produce the high-definition, high-resolution image.

10. The ultrasonic imaging apparatus of claim 7 wherein the weighting of the images provides a weighting for given data of at least one image dependent on a cumulative value of attenuating tissue traversed by the ultrasound beam in passing from the ultrasonic transducer to material located at a point of the given data.

11. The ultrasonic imaging apparatus of claim 7 wherein the weighting applies different weights to images of different frequencies with weighting of images with relatively higher frequencies decreasing with distance from the ultrasound transducer and the weighting of images with relatively lower frequencies increasing with distance from the ultrasound transducer.

12. The ultrasonic imaging apparatus of claim 7 including at least three images at different ultrasound frequencies wherein the weighting applies a constant weighting to an image of at least three images at an ultrasound frequency between frequencies of at least two other images.

13. The ultrasonic imaging apparatus of claim 7 wherein data for the images of different ultrasound frequencies are obtained in separate image acquisitions at different frequencies.

* * * * *